US010993655B2

(12) United States Patent
Swerdlow

(10) Patent No.: US 10,993,655 B2
(45) Date of Patent: May 4, 2021

(54) SYSTEM AND METHOD FOR SCREENING A PATIENT'S FOOT

(71) Applicant: Mark Swerdlow, Los Angeles, CA (US)

(72) Inventor: Mark Swerdlow, Los Angeles, CA (US)

(*) Notice: Subject to any disclaimer, the term of this patent is extended or adjusted under 35 U.S.C. 154(b) by 0 days.

(21) Appl. No.: 16/866,420

(22) Filed: May 4, 2020

(65) Prior Publication Data
US 2020/0345295 A1 Nov. 5, 2020

Related U.S. Application Data

(60) Provisional application No. 62/842,331, filed on May 2, 2019, provisional application No. 62/901,026, filed on Sep. 16, 2019.

(51) Int. Cl.
*G06K 9/00* (2006.01)
*A61B 5/00* (2006.01)
(Continued)

(52) U.S. Cl.
CPC ............ *A61B 5/447* (2013.01); *A61B 5/0022* (2013.01); *A61B 5/445* (2013.01); *A61B 5/6829* (2013.01); *A61B 5/749* (2013.01); *A61B 5/7425* (2013.01); *G06T 7/0016* (2013.01); *G16H 30/40* (2018.01); *G16H 40/67* (2018.01); *G16H 50/20* (2018.01); *G16H 50/30* (2018.01);
(Continued)

(58) Field of Classification Search
CPC ....... A61B 5/447; A61B 5/0022; A61B 5/445; A61B 5/6829; A61B 5/7425; A61B 5/749; A61B 2560/04; G16H 40/67; G16H 50/30; G16H 50/20; G16H 30/40; G06T 7/0016; G06T 2207/20084; G06T 2207/30004
See application file for complete search history.

(56) References Cited

U.S. PATENT DOCUMENTS 7,068,379 B2    6/2006 Sundman et al.
7,127,401 B2 *  10/2006 Miller .................... A61B 8/467
                                                   704/275
(Continued)

OTHER PUBLICATIONS

Smith-Strom et al., "Severity and Duration of Diabetic Foot Ulcer (DFU) Before Seeking Care as a Predictors of Healing Time: A Retrospective Cohort Study," PLOS One, 2017, 15 pages.
(Continued)

*Primary Examiner* — Shefali D Goradia
(74) *Attorney, Agent, or Firm* — Patterson Thuente Pedersen, P.A.

(57) ABSTRACT

A foot screening system configured to aid in screening a plantar surface of a foot of a user for sores, ulcers, and other signs of diseases. The foot screening system including a foot platform including a foot contacting surface configured to serve as a foot stabilizing device during a screening of a plantar surface of a foot of a user, a camera stabilizer platform configured to support a mobile computing device at a desired angle and distance from the foot platform, and a user interface configured to aid a user in capturing one or more images of the plantar surface of the foot of the user, flagging the one or more images for additional review, and uploading the one or more images to a network for access by a healthcare provider.

26 Claims, 14 Drawing Sheets

(51) Int. Cl.
*G16H 50/30* (2018.01)
*G16H 30/40* (2018.01)
*G16H 40/67* (2018.01)
*G06T 7/00* (2017.01)
*G16H 50/20* (2018.01)

(52) U.S. Cl.
CPC . *A61B 2560/04* (2013.01); *G06T 2207/20084* (2013.01); *G06T 2207/30004* (2013.01)

(56) References Cited

U.S. PATENT DOCUMENTS

| | | | |
|---|---|---|---|
| 9,019,359 B2 | 4/2015 | Leedy et al. | |
| 9,301,688 B2* | 4/2016 | Goldish | A61B 5/70 |
| 9,778,027 B1* | 10/2017 | Smith | A43D 1/025 |
| 2005/0097762 A1* | 5/2005 | Biesbrouck | A61B 5/1036 |
| | | | 33/3 R |
| 2012/0053490 A1* | 3/2012 | Smith | A61B 5/0082 |
| | | | 600/592 |
| 2013/0109951 A1* | 5/2013 | Goldish | A61B 5/0082 |
| | | | 600/407 |
| 2015/0077323 A1* | 3/2015 | Ramaswamy | G06F 3/0304 |
| | | | 345/156 |
| 2016/0029900 A1* | 2/2016 | LaPlante | A61B 5/6828 |
| | | | 600/335 |
| 2016/0183879 A1* | 6/2016 | Goldish | A61B 5/447 |
| | | | 600/474 |

OTHER PUBLICATIONS

Rowley et al, "Diabetes 2030: Insights from Yesterday, Today, and Future Trends," Population Health Management, vol. 20, No. 1, 2017, 7 pages.
Rice et al. "Burden of Diabetic Foot Ulcers for Medicare and Private Insurers," Diabetes Care, vol. 37, Mar. 2014, 8 pages.
"Detecting Objects in Images," The Sliding Window Method, date unknown, 12 pages.
Simeone et al., "Feet Movement in Desktop 3D Interaction," 9th Symposium on 3D User Interfaces, Mar. 2014, 4 pages.
Nike, "What is Nike Fit?," Nike News, May 9, 2019, 23 pages.

* cited by examiner

SYSTEM AND METHOD FOR SCREENING A PATIENT'S FOOT

RELATED APPLICATION INFORMATION

This application claims the benefit of U.S. Provisional Application No. 62/842,331 filed May 2, 2019 and 62/901,026 filed Sep. 16, 2019, the contents of which are fully incorporated herein by reference.

TECHNICAL FIELD

The present disclosure relates generally to a medical system for patients, and more particularly to a system and method for screening a foot of a patient for sores, ulcers, and other symptoms of diseases.

BACKGROUND

Diabetic foot ulcers are a major cause of morbidity, and their treatment is a financial burden on society. The longer patients live with diabetes, the more likely they are to develop peripheral neuropathy. Diabetics with peripheral neuropathy do not feel cuts or blisters; vascular and immunological insufficiencies impede wound healing and hasten progression of minor injuries to ulcers. Detecting and treating diabetic foot ulcers at an early stage is crucial for successful outcomes. However, many elderly, overweight, or inflexible patients cannot examine the soles of their feet and do not have anyone to check their soles regularly. Many diabetics can only realize they have a foot ulcer when the ulcer starts to drain into their socks.

Over 30 million Americans suffer from diabetes; this number is projected to reach 55 million by 2030. Up to 25% of diabetics will develop at least one ulcer; 6% of patients with ulcers will be hospitalized to treat an ulcer infection; and 20% of hospitalized patients will require amputation. Annual per-patient incremental health care expenditures for diabetic foot ulcers range from $12,000 to $17,000 (2014), and diabetics with foot ulcers utilize significantly more medical resource than those without ulcers. The vast majority of diabetes-related amputations are preceded by a foot ulcer. Thus, there is an important unmet need to diagnose diabetic foot ulcers early and monitor the effects of therapy efficiently.

Over the years various approaches to screening the bottom of a diabetic patient's foot have been developed. One such approach involves the use of a digital camera mounted in a box with a plurality of LEDs to illuminate and capture images of the bottom of the patient's foot. The images are then automatically sent on to a clinician for evaluation. This approach is generally disclosed in U.S. Patent Publ. No. 2005/0097762. Another approach involves the use of a patient standing on a glass platform while a scanner scans the bottom of the patient's foot. This approach is generally disclosed in U.S. Pat. No. 7,068,379. One notable drawback of this approach is that the plantar tissues are pressed against the glass, thereby producing artifacts that can be misinterpreted as callous tissue, or that can obscure the visualization of the earliest signs of skin breakdown (e.g., discoloration).

Another approach involves the use of a support frame configured to position a camera, smart phone, or other camera enabled tablet that captures images of the bottom of their foot which are sent to a separate display screen. This approach is generally disclosed in U.S. Pat. No. 9,301,688. One drawback of this approach is the need for two electronic components; notably a camera and a separate screen to view images. Further, without the use of a remote controller, operation of the camera is at best difficult.

SUMMARY OF THE DISCLOSURE

Embodiments of the present disclosure provide a system and method of screening a skin condition of a foot of a patient for wounds, ulcers, or other signs of diseases. In some embodiments, the system and method enable a constant and consistent position for foot placement, thereby enabling the patient to reliably and repeatedly screen a plantar surface of their foot, and to forward images of their foot to a healthcare provider for further review.

One embodiment of the present disclosure provides a method of screening a plantar surface of a foot of a user for calluses, abrasions, ulcers, and other signs of diseases. The foot screen method can include positioning a foot of the user on a foot platform and activating a screening assist program on a user interface of the mobile computing device. The foot screening method then includes positioning a mobile computing device on a camera stabilizer platform, and providing an initiation command to the mobile computing device to initiate a capture of one or more digital images of a plantar surface of a foot of the user. The foot screening method can include retrieving the mobile device from the camera stabilizer platform; and storing the one or more digital images in an archive database for comparison of the one or more digital images to past images or further review by a clinician.

One embodiment of the present disclosure provides a foot screening system configured to aid in screening a plantar surface of a foot of a user for sores, ulcers, and other symptoms of diseases. The foot screening system can include a foot platform, the camera stabilizer platform, and a screening assist program configured to be executed by a mobile computing device and provide a user interface. The foot platform can include a foot contacting surface configured to serve as a foot stabilizing device during a screening of a plantar surface of a foot of a user. The camera stabilizer platform can be configured to support a mobile computing device at a desired angle and distance from the foot platform. The user interface can be configured to aid a user in capturing one or more images of the plantar surface of the foot of the user, adding user data to the one or more images, such as flagging the one or more images for additional review, providing annotations of the one or more image, or adding time, date and notes about the health status of the user, and then uploading the one or more images to a network for access by a healthcare provider.

In one embodiment, the foot platform and the camera stabilizer platform can be operably coupled to one another via one or more extension rods. In one embodiment, the foot platform and the camera stabilizer platform can be configured to be spaced apart at one or more distances defined by one or more optical characteristics of the mobile computing device supported by the camera stabilizer platform. In one embodiment, the user interface can be configured to provide a recommended spacing between the foot platform and the camera stabilizer platform. In one embodiment, the foot platform can include a material cutout configured to house at least a portion of the camera stabilizer platform in a collapsed, storage position. In one embodiment, the foot platform can include a standardization indicator configured to enable postprocessing standardization of captured images. In one embodiment, the camera stabilizer platform can include a hinge configured to enable angular adjustment of a mobile computing device support surface relative to a horizontal frame of reference.

In one embodiment, the user interface can be configured to provide instruction for capturing one or more images of the plantar surface of the foot of the use. In one embodiment, the user interface can be configured to accept a first auditory signal to indicate a first image capture sequence, and a second auditory signal to initiate a second image capture sequence. In one embodiment, the user interface can be configured to provide a visual display of the first and second captured images for annotation by the user. In one embodiment, the user interface can be configured to enable comparison of two or more captured images.

In one embodiment, the system can be configured to utilize image data falling outside of the visible light spectrum in the detection of a sore on the plantar surface of the foot of the user before an emergence of the sore becomes visually detectable. In one embodiment, the system can further include a neural network configured to aid in classification of images captured by the system.

In one embodiment, the foot platform and the camera stabilizer platform can be operably coupled to one another via one or more extension rods. In one embodiment, the foot platform and the camera stabilizer platform can be operably coupled to one another via one or more extension rods and are configured to be spaced apart at a distance defined by one or more optical characteristics of the mobile computing device supported by the camera stabilizer platform. In one embodiment, the foot platform can include a material cutout configured to house at least a portion of the camera stabilizer platform in a collapsed, storage position. In one embodiment, the foot platform can include a standardization indicator configured to enable postprocessing standardization of captured images.

In one embodiment, the method can further include analyzing image data falling outside of the visible light spectrum to detect a sore on the plantar surface of the foot of the user before an emergence of the sore becomes visually detectable. In one embodiment, the method can further include using a neural network to aid in classification of images captured by the system. The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1A:
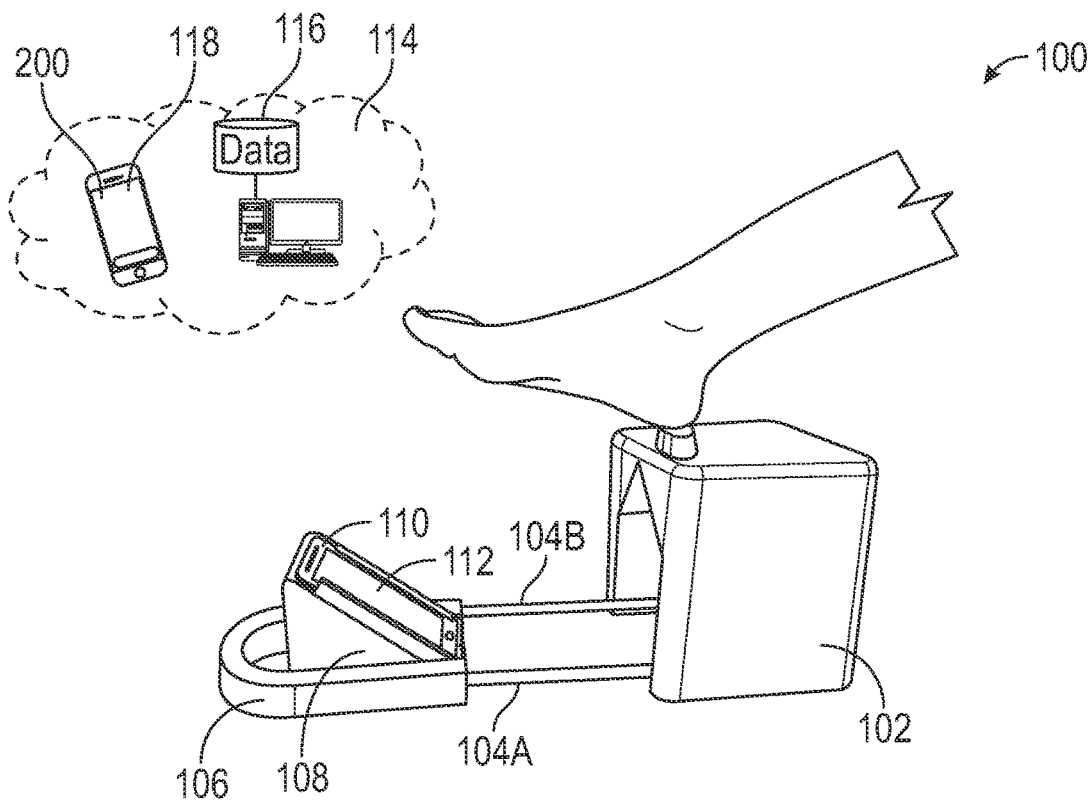
FIG. 1A is a system diagram depicting a foot screening system with a heel of a user positioned on a foot platform, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1B:
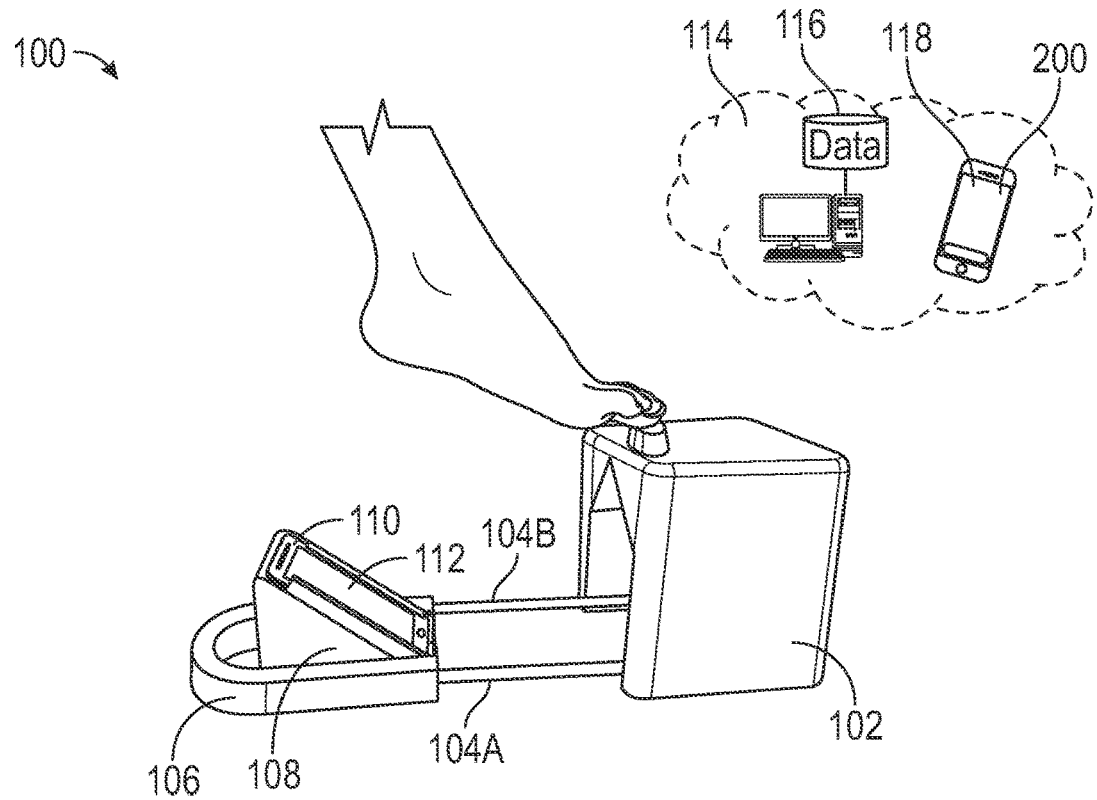
FIG. 1B is a schematic diagram depicting a foot screening system with a toe of a user positioned on a foot platform, in accordance with an embodiment of the disclosure.

Referring to FIGS. 1A-1B, a foot screening system 100 for screening a skin condition of a foot of a patient for sores, ulcers, or other symptoms of disease is depicted in accordance with an embodiment of the disclosure. In some embodiments, the system 100 can include a foot platform 102, one or more extension rods 104, base 106, and a camera stabilizer platform 108. In some embodiments, the system 100 can further include a mobile computing device 110 (e.g., cellular telephone, tablet, etc.). In other embodiments, the camera stabilizer platform 108 (alternatively referred to as an optical platform 108) can include a camera, wireless transmission electronics and a screen, which can optionally be in communication with the mobile computing device 110. In some embodiments, the mobile computing device 110 can be configured to operate a plantar screen assist program 200 (as discussed in greater detail below), which can include a user interface 112. In some embodiments, the mobile computing device 110 can be in communication with a network or cloud computing platform 114 configured to store digital images captured by the mobile computing device 110 in an archive database 116 and/or send the one or more captured images to a remote display 118. Various embodiments of the system 100 will be described in detail with reference to the figures, wherein like reference numerals represent like parts and assemblies throughout the views.

Figure 2A:
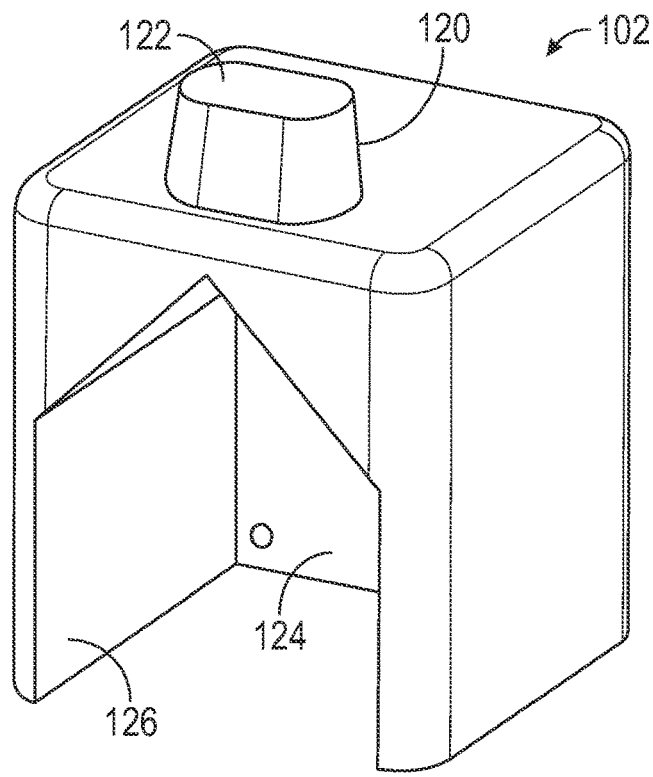
FIG. 2A is a perspective view depicting a foot platform, in accordance with an embodiment of the disclosure.

With additional reference to FIG. 2A, the foot platform 102 can be configured to enable a user to position a distal portion of their lower extremity (e.g., toe, heel, other portion of foot, amputated stump, etc.) on the platform 102 for a screening of the plantar surface of the user's foot. In one embodiment, the foot platform 102 can include a frustum 120 configured to support a portion of the user's foot. For example, in some embodiments, the frustum 120 can be configured to support at least a rear portion of the user's foot (e.g., the calcaneus) (as depicted in FIG. 1A), or a front portion of the user's foot (e.g., the metatarsals or phalanges) (as depicted in FIG. 1B). In some embodiments, the frustum 120 can generally have an oval shaped top surface 122, which in some embodiments can measure about 60 mm wide by about 40 mm tall. Other frustum 120 shapes and sizes are also contemplated, including frustum 120 configurations adapted to users with lymphedema, elephantiasis, morbid obesity, and other conditions. For example, in some embodiments, the top surface 122 of the frustum 120 can be in the shape of a circle, oval, polygon, rounded polygon, trefoil, or other shape.

Additionally, although the top surface 122 is depicted as being flat, in other embodiments, the top surface 122 can include a depression or other contour configured to conform to a portion of the user's foot. In some embodiments, the top surface 122 can be constructed of a semi-conformable material, configured to conform to the contours of a user's foot. The use of rails, guides or other supports to encourage a proper positioning of a user's foot is also contemplated. In some embodiments, portions of the frustum 120 can be clear or at least partially transparent to minimize interference with a screening of the plantar surface of the user's foot. In one embodiment, the foot platform can be adjustable in height to optimally position the user's foot during screening. In one embodiment, the frustum 120 can lock into place for use and unlock to be pushed down into foot platform 102 so as not to extend past an upper plane of foot platform 102.

Figure 3A:
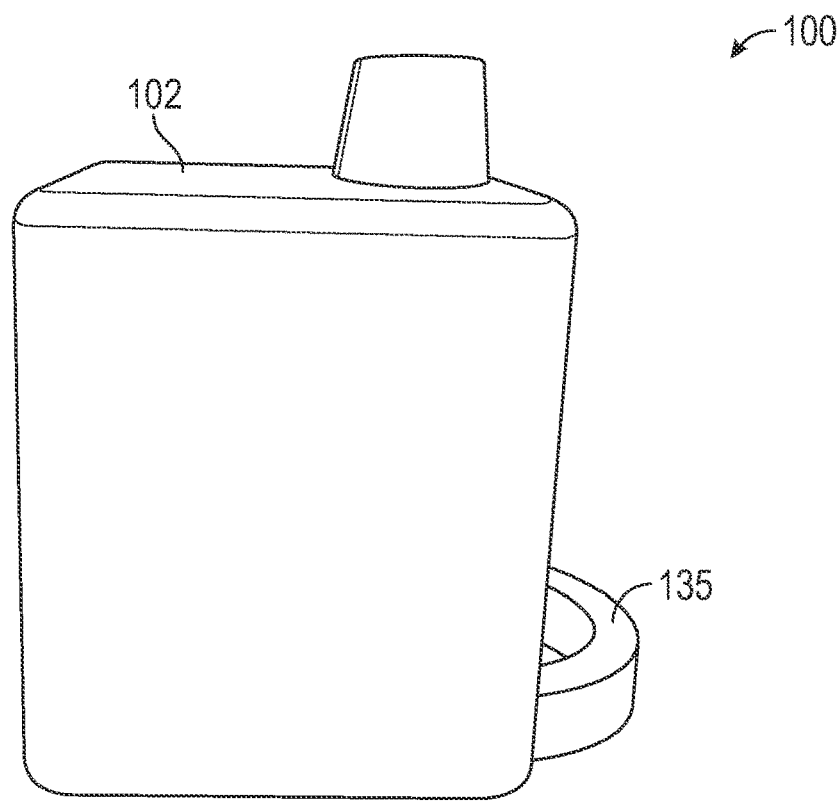
FIG. 3A depicts a foot screening system in a collapsed, storage position, in accordance with an embodiment of the disclosure.
Figure 3B:
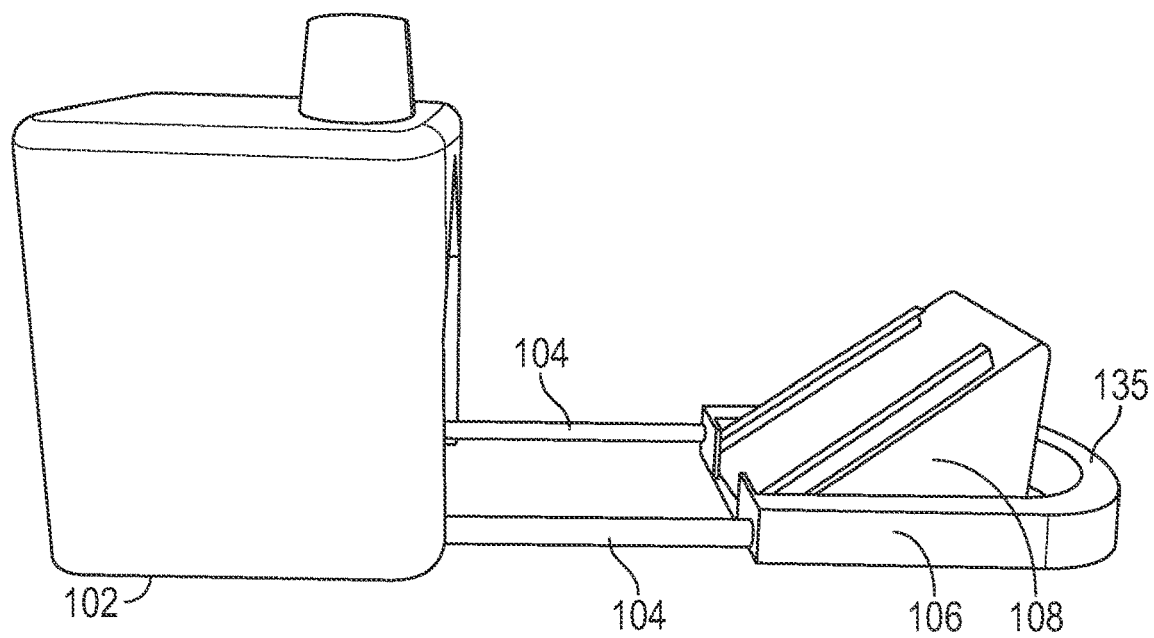
FIG. 3B depicts a foot screening system in an expanded, in use position, in accordance with an embodiment of the disclosure.

The one or more extension rods 104A/B can be operably coupled to the foot platform 102 at a rear wall 124, thereby enabling the base 106 and camera stabilizer platform 108 to shift or translate relative to the foot platform 102 between a collapsed, storage position (as depicted in FIG. 3A), and an expanded, in use position (as depicted in FIG. 3B). For example, in one embodiment, the foot platform 102 can include structure defining a material cut out 126, thereby enabling the base 106 and/or camera stabilizer platform 108 to be at least partially housed within the foot platform 102. Although various shapes and configurations of the foot platform 102 are contemplated, in one embodiment, the foot platform 102 can generally be in the shape of a box, for ease in transportation and storage. In some embodiments, the foot platform 102 can further include a handle (not depicted) which can optionally be folded into a cut out on the platform 102 for ease in carrying and/or otherwise manipulation of the foot screening system 100.

In some embodiments, the one or more extension rods 104A/B can be telescoping in nature, thereby enabling a user to adjust a distance between the foot platform 102 and the camera stabilizer platform 108 to accommodate for imaging characteristics of a variety of mobile computing devices 110. In some embodiments, the one or more extension rods 104A/B can include one or more markings, detents, or other indicators for ideal extension. In some embodiments, the one or more markings can be based on the optical characteristics (e.g., f-stop, aperture, shutter speed, etc.) of the camera included in the mobile computing device 110. For example, in some embodiments, the extension rods 104A/B can be configured with a first marking at approximately 90 mm (e.g., to accommodate large devices, iPhone Plus/Max, etc.), a second marking at approximately 125 mm (e.g., to accommodate medium devices, iPhone X, etc.), and a third marking at approximately 140 mm (e.g., to accommodate small devices, iPhone 6, 7, 8, etc.); additional markings at other distances are also contemplated. In some embodiments, length adjustment of the extension rods 104 can be manual. In other embodiments, length adjustment can be made at least partially autonomously via the plantar surface screening assist program 200.

Figure 2B:
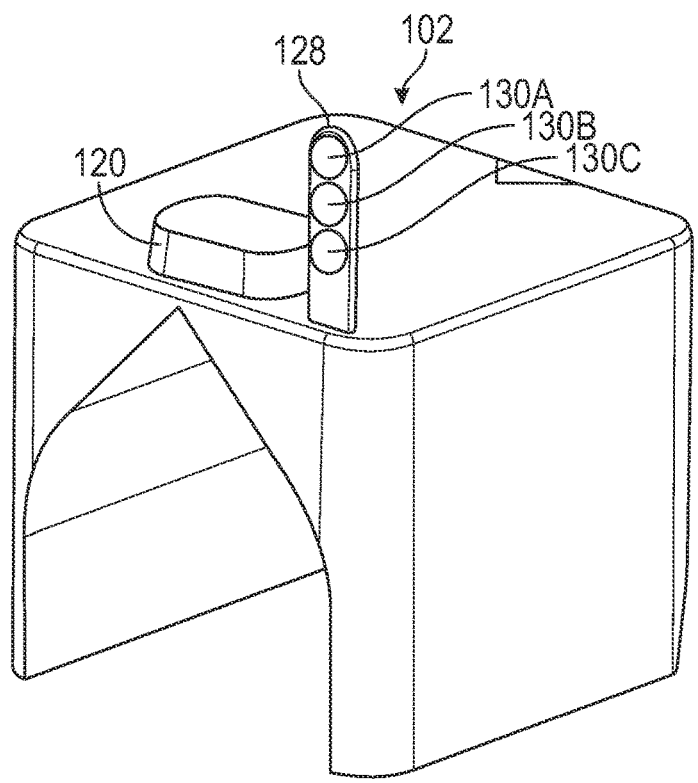
FIG. 2B is a perspective view of a foot platform including a standardization indicator, in accordance with an embodiment of the disclosure.

With reference to FIG. 2B, in some embodiments, the foot platform 102 can include a standardization indicator 128 configured to enable post-processing standardization of the images. In some embodiments, the standardization indicator 128 can be added to the foot platform 102 such that the standardization indicator 128 is configured to be positioned in the same place in every image. The standardization indicator 128 can include one or more markers 130A-C to aid in post-processing standardization of the images, such as colored markers 130A-C (e.g., red, green and blue markers) to aid adjustment of coloration and hue, reflectors to aid in adjustment of lighting or brightness conditions, as well as other tools to aid in image processing. In some embodiments, the standardization indicator 128 can be configured to provide a sizing frame of reference as an aid in determining a size of the user's foot or wounds, as well as relative distances, such as a wound diameter or distance between wounds, in the images. The standardization indicator 128 may fold into the upper surface of foot platform 102.

Figure 4:
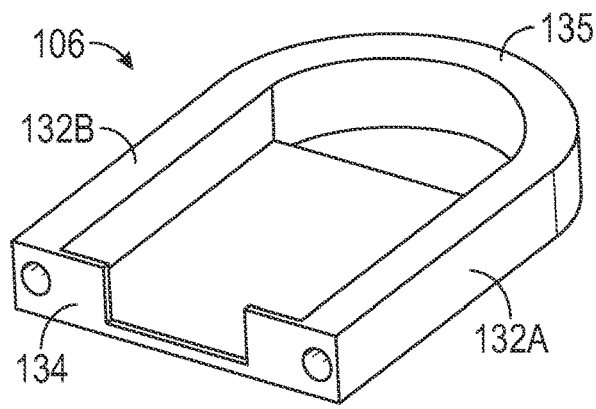
FIG. 4 is a perspective view depicting a base, in accordance with an embodiment of the disclosure.

With continued reference to FIG. 1A, the base 106 can be operably coupled to the foot platform 102 via the one or more extension rods 104A/B, thereby enabling the distance of the base 106 and camera stabilizing platform 108 to be adjusted relative to the foot platform 102. With additional reference to FIG. 4, in some embodiments, the base 106 can include one or more base walls 132A/B configured to couple to the one or more extension rods 104A/B. An anterior wall 134, together with the base walls 132A/B, can be configured to retain the camera stabilizer platform 108 in position relative to the base 106. In some embodiments, the base 106 can further include a grip 135 as an aid in manipulating the base 106 relative to the foot platform 102. For example, in one embodiment, the grip 136 can be configured as a curved handle configured to protrude from the foot platform 102 when the foot screening system 100 is in the collapsed, storage position (as depicted in FIG. 3A). Other configurations of the grip 135 are also contemplated.

Figure 5A:
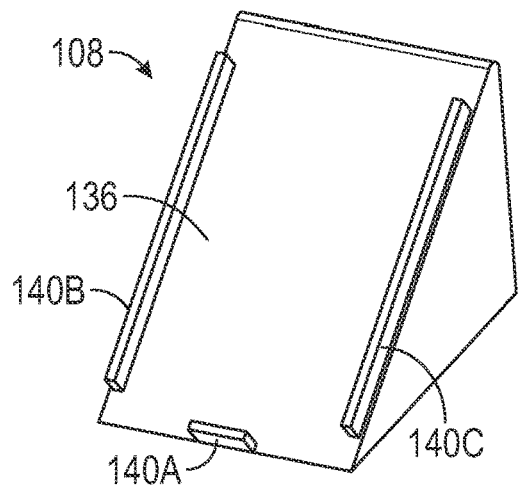
FIG. 5A is a perspective view depicting a camera stabilizer platform, in accordance with an embodiment of the disclosure.

With additional reference to FIG. 5A, the camera stabilizer platform 108 can include a support surface 136 configured to support the mobile computing device 110 at an inclined angle relative to a surface on which the platform 108 is positioned, thereby providing a view of the plantar surface of the user's foot. In some embodiments, the angle of the support surface 136 can be fixed relative to a horizontal frame of reference. For example, in one embodiment, the support surface 136 can have an angular orientation of about 38 degrees.

Figure 5B:
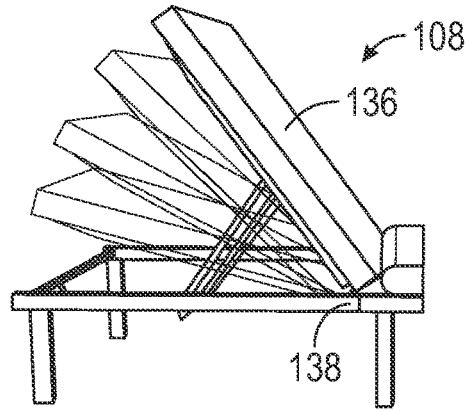
FIG. 5B is a perspective view depicting the camera stabilizer platform including a hinge for angular adjustment, in accordance with an embodiment of the disclosure.

In other embodiments, the support surface 136 can be adjustable such that the support surface 136 can be positioned to be substantially parallel to the plantar surface of the patient's foot regardless of the position of the user. For example, with reference to FIG. 5B, in some embodiments, the camera stabilizer platform 108 can include one or more hinges 138 configured to enable angular adjustment of the support surface 136 relative to a surface on which the platform 108 is positioned. In some embodiments, the one or more hinges 138 can be configured to enable angular adjustment of the support surface 136 in a range of between about 20-60 degrees relative to a horizontal frame of reference; although other adjustment angles are also contemplated. In some embodiments, angular adjustment of the support surface 136 can be manual. In other embodiments, angular adjustment can be made at least partially autonomously via the plantar surface screening assist program 200.

Figure 5C:
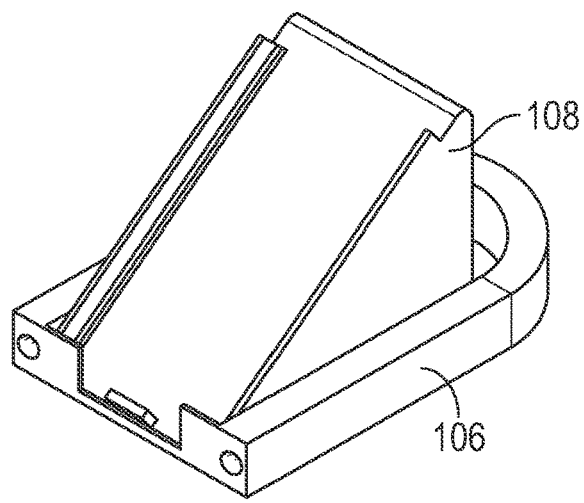
FIG. 5C is a perspective view depicting a unitary base and camera stabilizer platform, in accordance with an embodiment of the disclosure.

As depicted in FIG. 5A, in some embodiments, camera stabilizer platform base 108 can include one or more ledges 140A-C configured to aid in positioning and retention of the mobile computing device 110 within the camera stabilizer platform 108. In some embodiments, the one or more ledges 140A-C can be adjustable to accommodate a variety of different sizes and shapes of mobile computing devices 110. In some embodiments, the camera stabilizer platform 108 can be retained within the base 106 (e.g., via base walls 132A/B and/or anterior wall 134). With reference to FIG. 5C, in another embodiment, the base 106 and camera stabilizer platform 108 can be constructed as a single integrated unit.

Figure 6A:
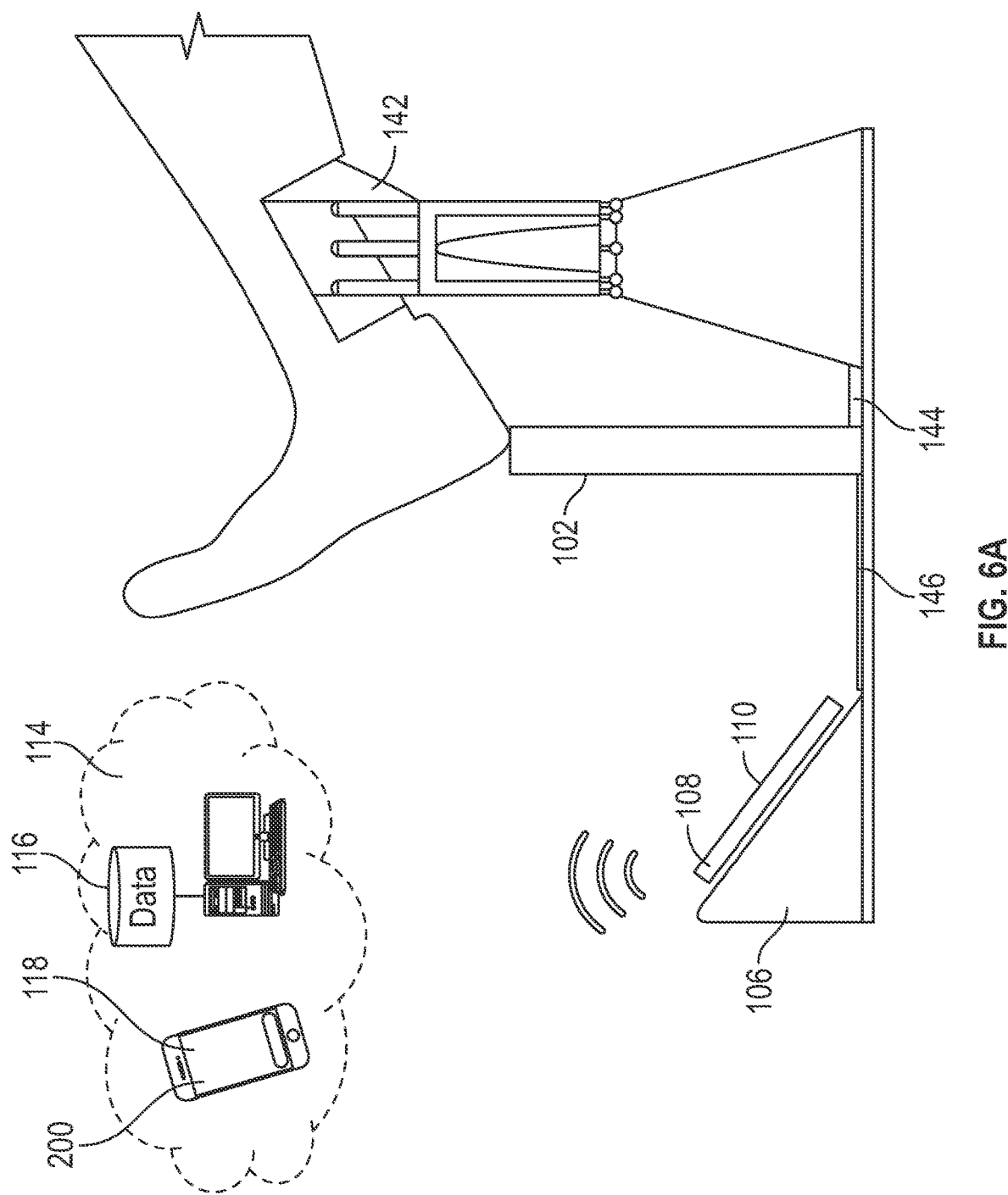
FIG. 6A is a schematic view depicting a foot screening system including a lower leg support structure, in accordance with an embodiment of the disclosure.
Figure 6B:
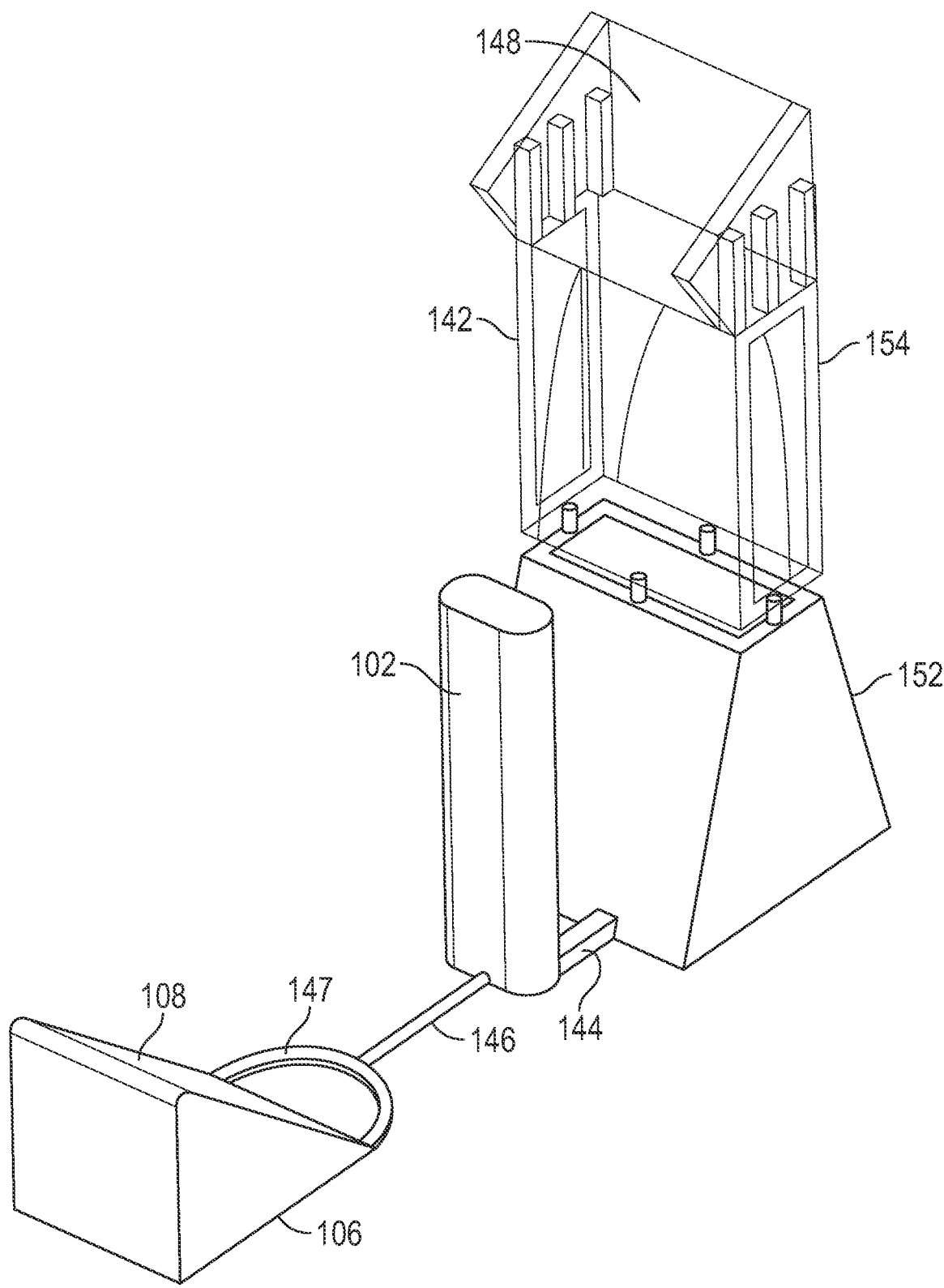
FIG. 6B is a perspective view depicting a portion of the foot screening system of FIG. 6A.

Referring to FIGS. 6A-B, another embodiment of a foot screening system 100 is depicted in accordance with an embodiment of the disclosure, wherein like reference numerals represent like parts and assemblies among the embodiments. As depicted, the foot screening system 100 can include a foot platform 102 and a camera stabilizer platform 108, similar to that described in the embodiments depicted in FIGS. 1-5. Additionally, in some embodiments, the foot screening system 100 can include a lower leg support structure 142, and one or more optional spacers 144, 146 for ideal positioning of the camera stabilizer platform 108, foot platform 102, and lower leg support structure 142 relative to one another.

In one embodiment, the lower leg support structure 142 can include a "U" shaped support 148 configured to cradle a portion of the patient's lower leg in proximity to the patient's ankle. For example, in one embodiment, the lower leg support can be configured to support the medial malleolus and lateral malleolus of the patient. The lower leg support structure 142 can include a base 152 and an extension 154. Collectively, the lower leg support structure 142 can be configured to optimally position a leg of the patient in a desired position relative to the camera stabilizer platform 108 on which the mobile computing device 110 is positioned during screening. In some embodiments, a length of the extension 154 can be matched to a size of the user (e.g., S, M, L, XL, XXL), to ensure optimal positioning of the user's foot relative to the camera stabilizer platform 108. Advantageously, the lower leg support structure 142 and support tower can be disassembled for ease in storage and transportation when not in use.

A first spacer 144 can be positioned between the lower leg support structure 142 and the foot platform 102. In some embodiments, the length of the first spacer 144 can be adjustable to accommodate the size of the user. A second spacer 146 can be positioned between the foot platform 102 and the camera stabilizer platform 108 (which in some embodiments can be integrally formed with base 106). The second spacer 146 can be configured to optimally position the camera stabilizer platform 108 relative to the foot platform 102, thereby enabling a full view of the plantar surface of the user's foot while providing an ideal focal distance for capturing digital images thereof. As depicted, in one embodiment, the spacer 146 can include a semi-circular component 147 configured to aid in support of the mobile computing device 110 in a lateral or vertical orientation. In some embodiments, the second spacer 146 can be operably coupled to the camera stabilizer platform 108, for example in the form of an extension rod.

In some embodiments, a distance between the foot platform 102 and the camera stability platform 108 can be manually adjusted. Alternative embodiments include the addition of mechanical or electrical features to optimize the distance between the foot platform 102 and the camera stability platform 108. For example, the spacer 146 and/or extension rods 104 can include electronics configured to measure the distance between the camera stabilizer platform 108 and the foot platform 102 and indicate to the user (e.g., via lights, sounds, etc.) whether repositioning of the camera stabilizer platform 108 is desirable. In another embodiment, strings or tabs can be included to provide a static measurement configured to aid users when extending the spacer 146 and/or extension rods 104 to ensure that the camera stabilizer platform 108 can repeatedly be placed in the correct position relative to the foot platform 102.

Figure 7:
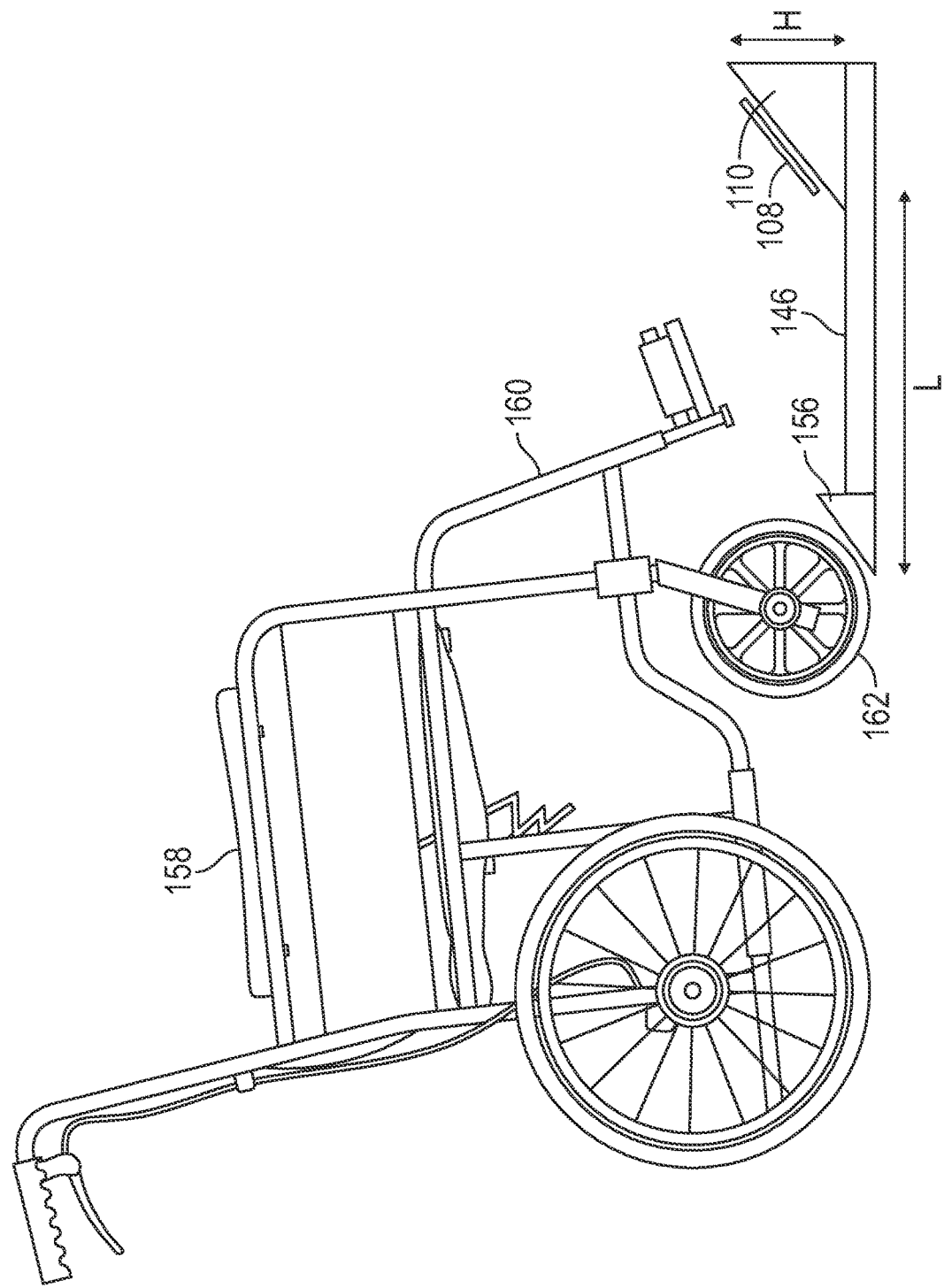
FIG. 7 is a schematic view depicting a foot screening system for wheelchair-bound users, in accordance with an embodiment of the disclosure.

Referring to FIG. 7, a foot screening system 100 adapted for use by users in a wheelchair 158, is depicted in accordance with an embodiment of the disclosure. Like the previous embodiments, like reference numerals represent like parts and assemblies among the various embodiments. As depicted, the foot screening system 100 can include a camera stabilizer platform 108, spacer 146 and wheelchair wedge 156. The wheelchair 158 can include lower leg support 160, which in some embodiments can be used in place of the foot platform 102. Accordingly, in some embodiments, a user can position a wheel 162 of the wheelchair 158 against the wheelchair wedge 156, thereby positioning their foot relative to the camera stabilizer platform 108 for screening. Thereafter, the user can activate the plantar surface screening assistance program 200 to initiate screening.

Figure 8:
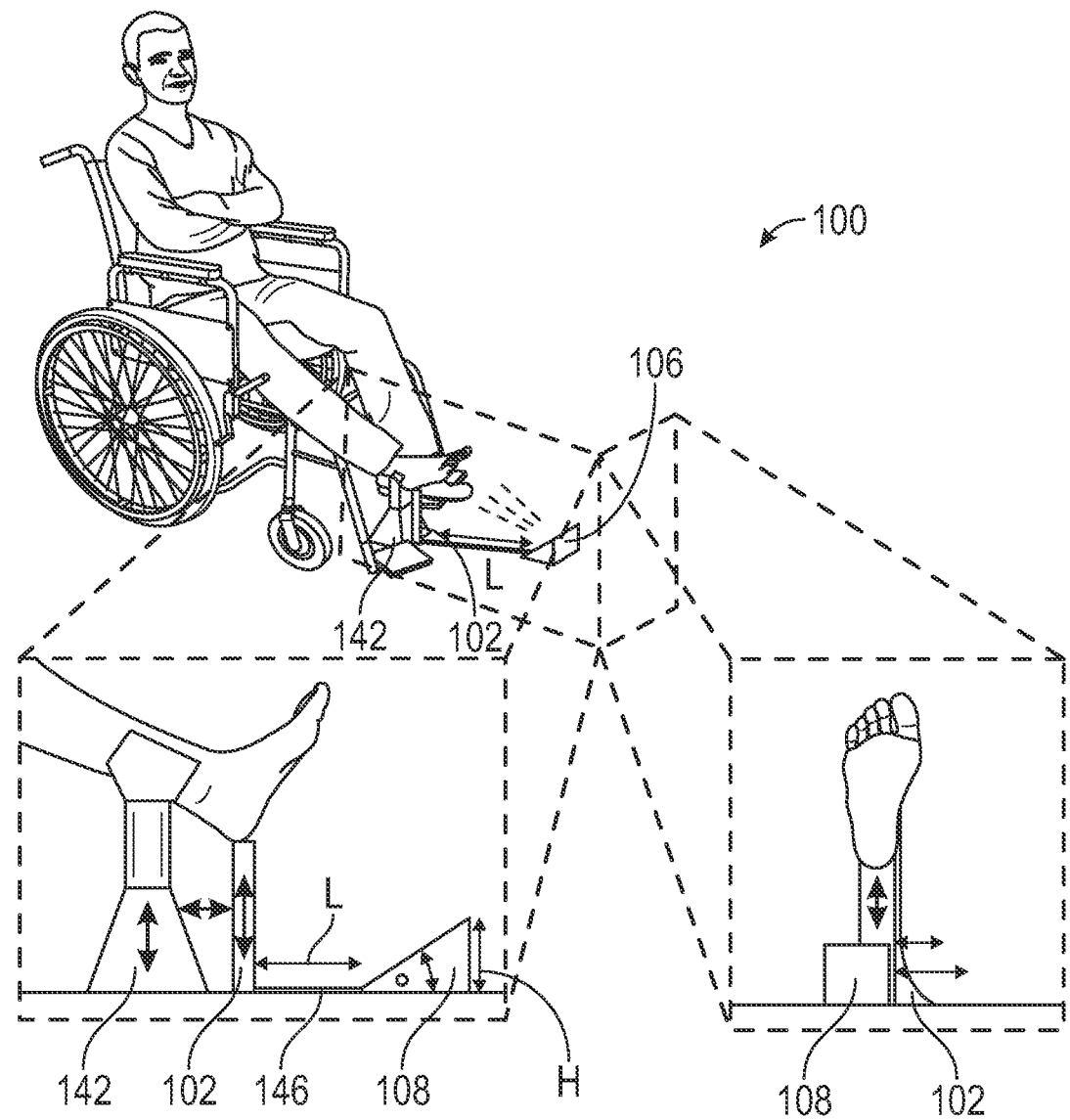
FIG. 8 is a schematic diagram depicting adjustment of the foot screening system, in accordance with an embodiment of the disclosure.
Figure 9:
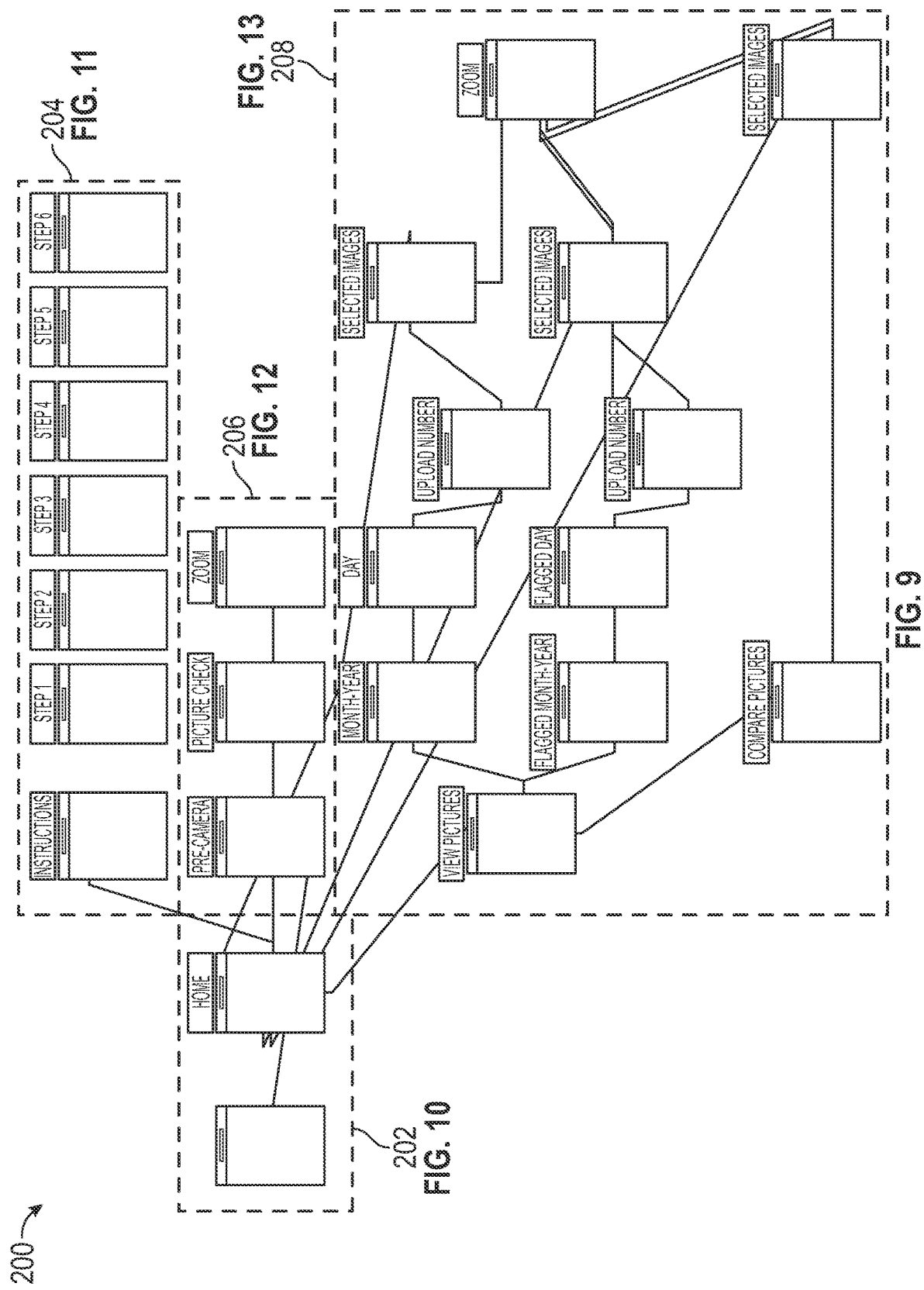
FIG. 9 is a flowchart depicting a plantar surface screening assist program, in accordance with an embodiment of the disclosure.

In some embodiments, a known distance and relative orientation between the bottom of the user's foot and the camera stabilizer platform can be utilized by the system 100 to improve and standardize imaging of the user's foot. For example, with reference to FIG. 8, in some embodiments, the plantar surface screening assist program 200 can assist in positioning of the user's foot and/or configuration of the foot screening system 100 (e.g., adjusting a distance of the one or more extension rods 104/spacer 146 and/or angular adjustment of the support surface 136 of the camera stabilizer platform 108) prior to screening.

In one embodiment, user positioning and/or system configuration specifications can be determined by the plantar surface screening assist program 200 based on one or more images of an initial positioning of user's leg and foot taken from one or more perspectives. For example, in one embodiment, the plantar surface screening assist program 200 can utilize side and frontal images to determine one or both of a spacing distance (L) of the user's foot (e.g., foot platform 102) from the camera stabilizer platform 108, and an inclination angle of the camera stabilizer platform 108 (e.g., based on an adjustable height (H) of the back of the camera stabilizer platform 108). The determination of other distances and angles are also contemplated. For example, in an initial set of images, a distance reference, such as a measuring stick, or a set of fiducial markers which are determined to be of a known distance are used to scale the image of the wheelchair to determine both the dimensions, positions and angles of the foot, in addition to the distances for L and H to achieve a desirable and repeatable image of a plantar surface of the user's foot. In some embodiments, the plantar surface screening assist program 200 can be configured to test/confirm whether the entire plantar surface of the user's foot is captured in the image. In some embodiments, the specific model of the mobile computing device 110 and/or optical characteristics of the imaging source (e.g., f-stop, aperture, shutter speed, etc.) can be considered in determining distances for L and H to achieve a desirable and repeatable image of a plantar surface of the user's foot. In some embodiments, the system 100 can utilize a lookup table as an aid in determining distances and angles for a specific imaging source and/or mobile computing device 110. A user can then adjust the camera stabilizer platform 108 and other components of the system 100 as determined by the screening assist program 200.

With reference to FIG. 9-13, a flowchart for a plantar surface screening assist program 200 is depicted in accordance with an embodiment of the disclosure. In one embodiment, the plantar surface screening assist program 200 can include a login portion 202 (depicted in FIG. 10), an instructional portion 204 (depicted in FIG. 11), an image capture portion 206 (depicted in FIG. 12), and a review, storage and further analysis portion 208 (depicted in FIG. 13). Collectively, these portions of the plantar surface screening assist program 200 can cooperate to enable the screening of a skin condition of a foot.

Figure 10:
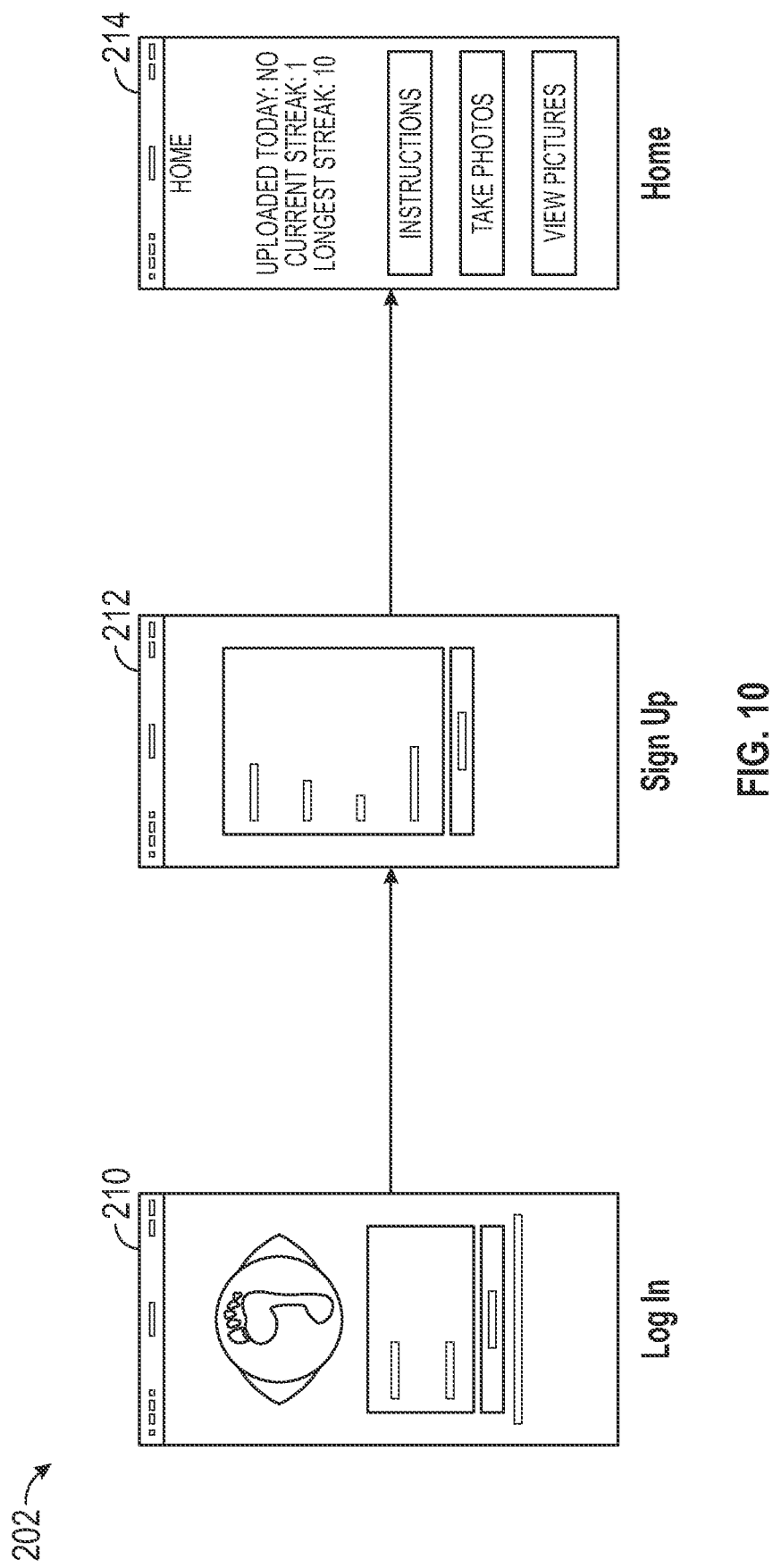
FIG. 10 is a flowchart depicting a login portion of a plantar surface screening assist program, in accordance with an embodiment of the disclosure.

With reference to FIG. 10, in the login portion 202, users are initially taken to a login screen 210 where a user can enter their login credentials (e.g., username, password, etc.). If no login credentials have been established, the user can be directed to a sign-up screen 212 configured to walk the user through the process to create an account, including selection of a username and password. Once the user has created an account and logged in, the plantar surface screening assist program 200 can display a home screen 214, presenting the options of: (1) reviewing instructions for system 100 operation and/or operation of the plantar surface screening assist program 200; (2) initiating an image capturing sequence; and/or (3) viewing or reviewing archived screening images. Although three options are depicted, the presentation of a greater or lesser number of options is also contemplated. For example, an additional option to send or view a message to a healthcare provider is also contemplated.

Figure 11:
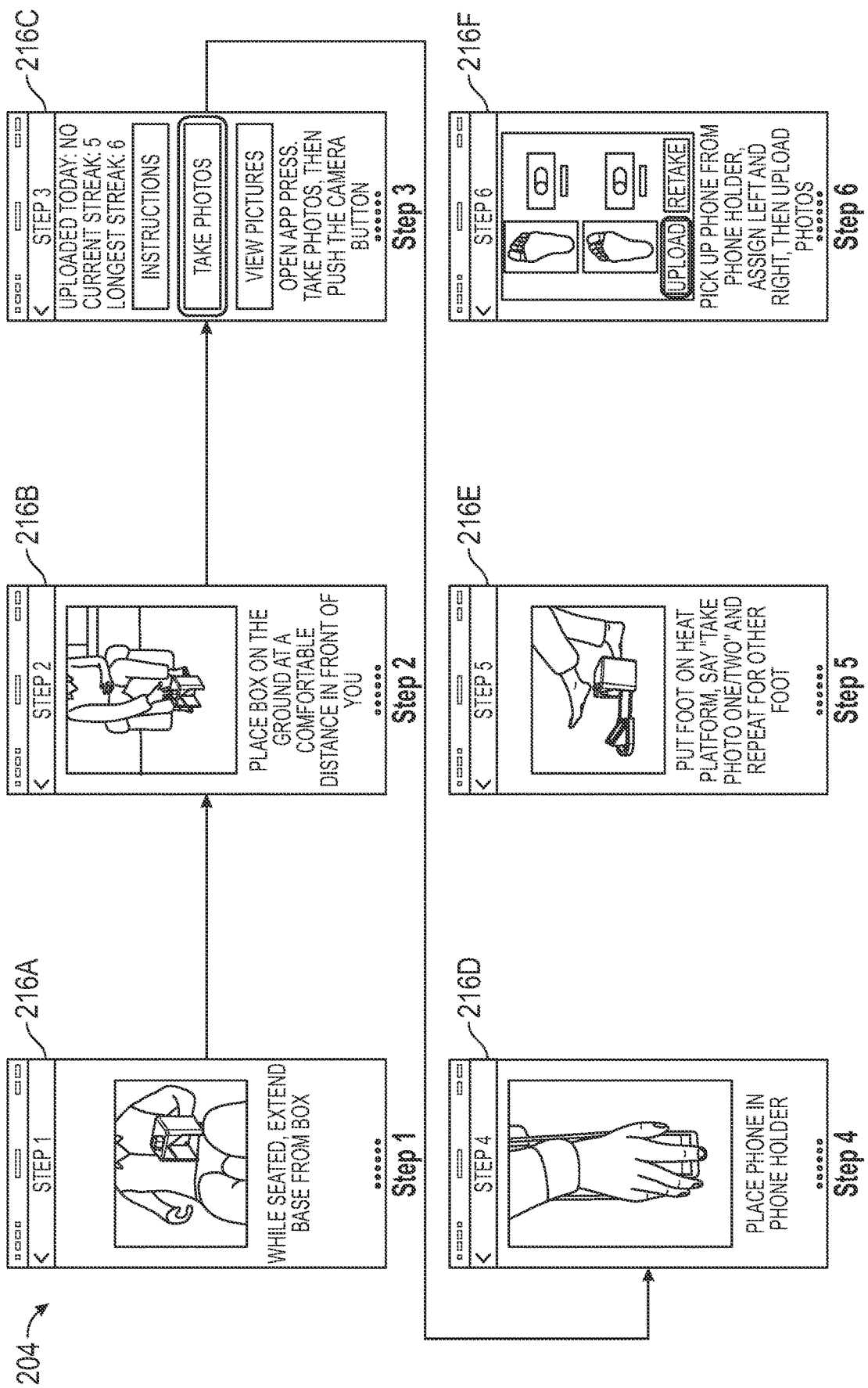
FIG. 11 is a flowchart depicting an instructional portion of a plantar surface screening assist program, in accordance with an embodiment of the disclosure.

Selection of the option of reviewing instructions initiates the instructional portion 204 of the plantar surface screening assist program 200. With reference to FIG. 11, the instructional portion 204 can present one or more instructional screens 216A-F with instructional information, such as a series of steps for which the user is to perform in order to complete the screening process. Although six screens 216A-F are depicted, a greater or lesser number of instructional screens are also contemplated.

Figure 12:
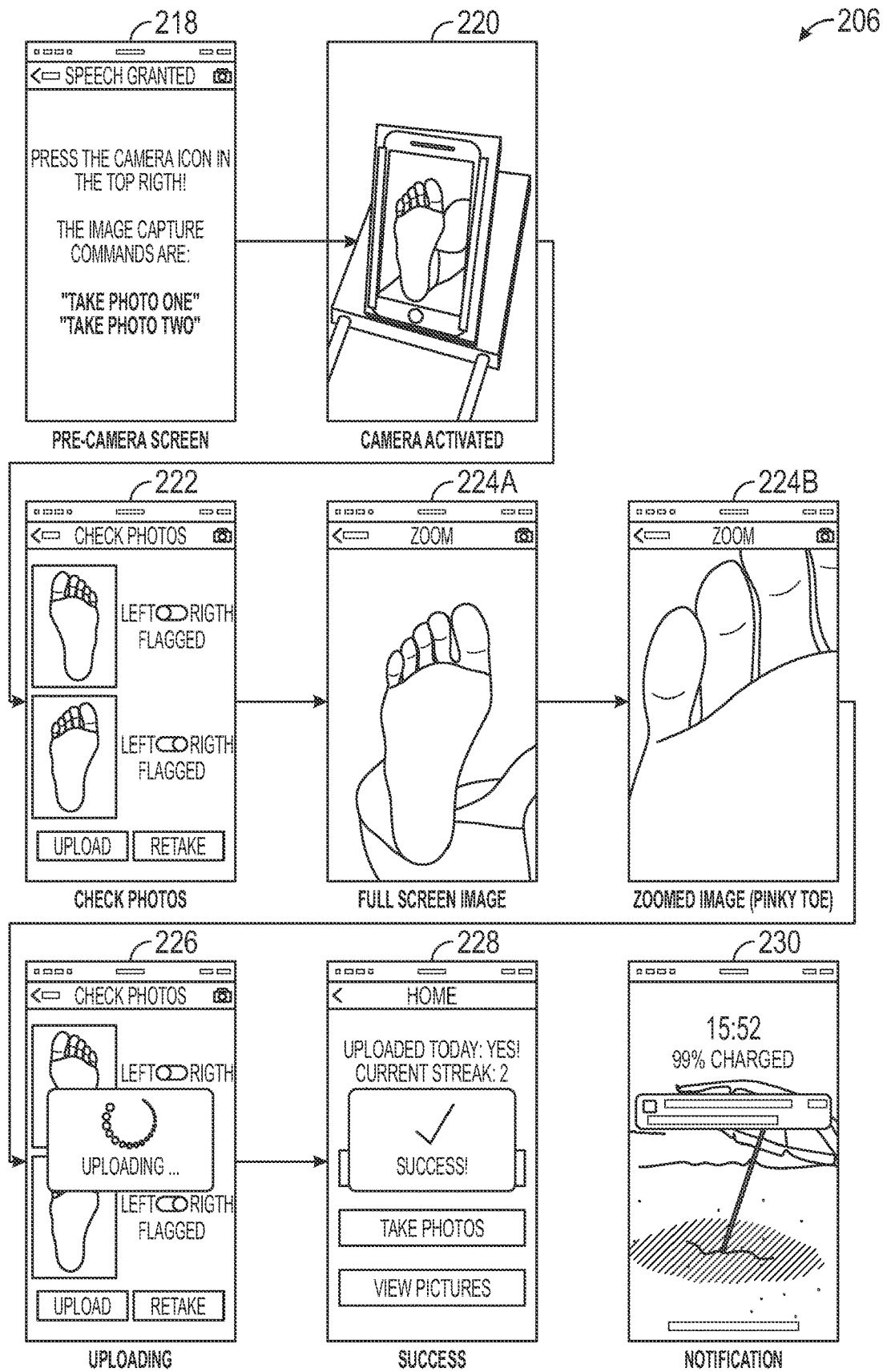
FIG. 12 is a flowchart depicting an image capture portion of a plantar surface screening assist program, in accordance with an embodiment of the disclosure.

Selection of the option of initiating the image capturing sequence initiates the image capture portion 206 of the plantar surface screening assist program 200. With reference to FIG. 12, the image capture portion 206 can initially present a user with a pre-camera screen 218 featuring image capture instructions, such as to position the mobile computing device 110 on the camera stabilizer platform 108, and when ready provide an initiation command to the mobile computing device 110 to initiate capture of one or more digital images of a plantar surface of the foot of the user.

In one embodiment, the initiation command can be voice-activated, such as by stating the phrase "take photo one," "take photo two," or some other verbal command. In one embodiment, the initiation command can be activated by a sound, such as a clap, snap or the like in which a microphone within the mobile computing device 110 is configured to trigger initiation of an image capture sequence. In one embodiment, the initiation command can be triggered via a Bluetooth remote or another method of remotely initiating the image capture on camera enabled devices. In one embodiment, the initiation command can be triggered via a Wi-Fi connection, in which a user could visit a website and press a "take photo" button to trigger image capture.

Thereafter, at 220, the camera of the mobile computing device 110 can be activated. Once one or more digital images have been captured, the user can retrieve the mobile computing device 110. At 222, the user can be given the option of assigning observational data to the one or more digital images via the user interface 112. For example, in one embodiment, the user can select either the left foot or right foot for notation, along with a digital flag for additional review, comments, or follow-up. Alternatively, after an initial review of the captured digital images, the user can opt to retake the one or more digital images. At 224A-B, a user can view a full-screen image of the photograph, with the option to zoom into areas of interest.

Once the user is satisfied with the captured images, and any desirable observational data has been noted, at 226, the one or more images can be uploaded to the cloud computing platform 114, where the images can be stored in the archive database 116 with an appropriate date and time stamp for chronological organization. At 228, the user can be notified of the successful uploading of the one or more images to the cloud computing platform 114. Thereafter, the user can be redirected to the home screen, which can be updated to indicate the number of photos that the user has successfully uploaded. In some embodiments, a user can be provided with a reminder or notification 230 if the user has not successfully uploaded images according to a defined schedule.

Figure 13:
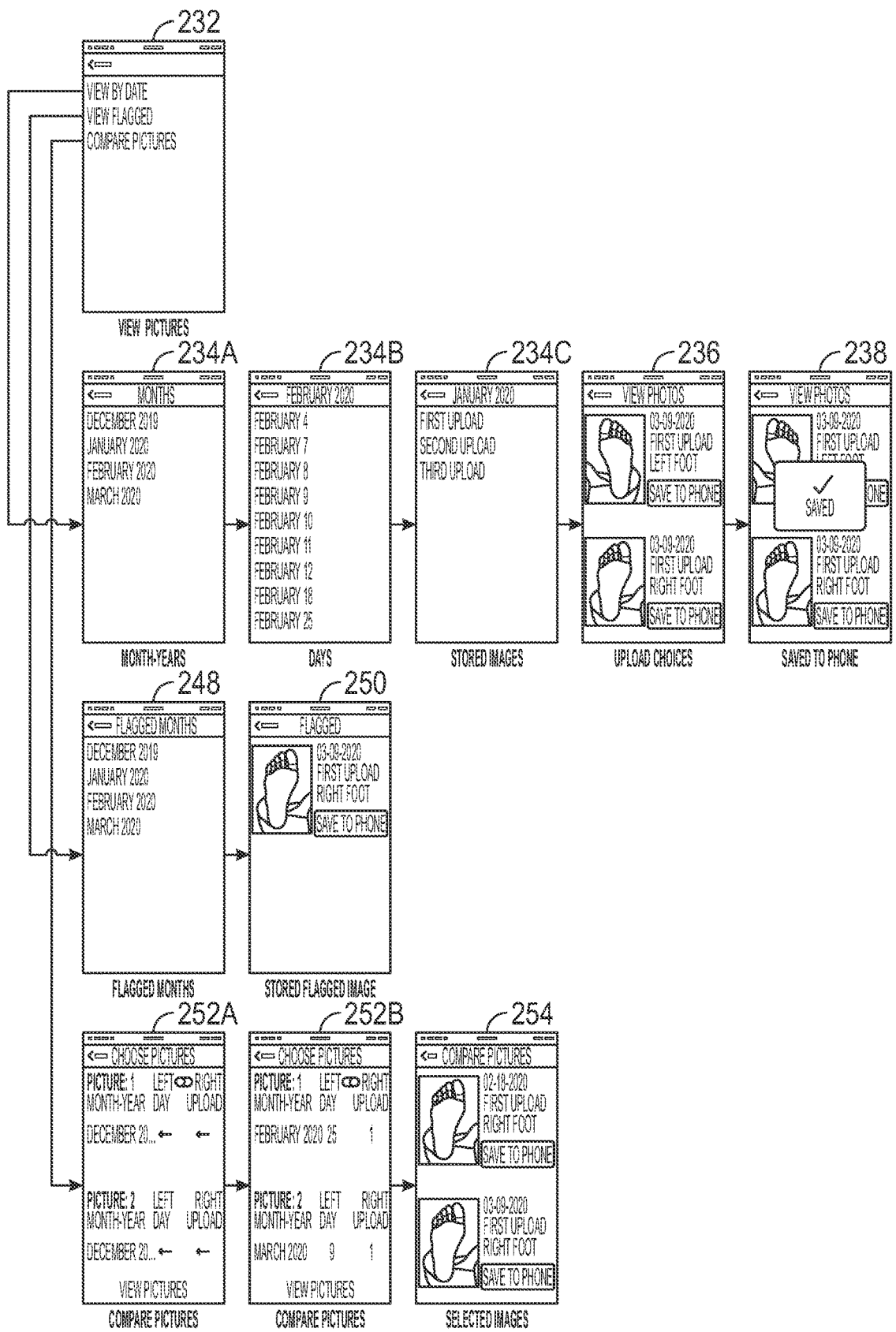
FIG. 13 is a flowchart depicting a further analysis portion of a plantar surface screening assist program, in accordance with an embodiment of the disclosure.

The one or more digital images uploaded to the cloud computing platform 114 can be accessed by the analysis portion 208 of the plantar surface screening assist program 200. With reference to FIG. 13, the analysis portion 208 can present the user with the option to review recently stored images. For example, in one embodiment, at 232, the user can be presented with the options of viewing stored images according to their date/time stamp, viewing flagged images only, or comparing two or more images.

If a user selects the option to review recently stored images, at 234A-C, the user can select the month/year, day, and/or upload on that day (e.g., first upload, second upload, third upload, etc.), for viewing of the captured images. A calendar view with days containing uploads highlighted is also contemplated. At 236, the stored images can be viewed, with the option of saving the one or more images to the mobile computing device 110. If the user selects the option of saving the one or more images, at 238, a notification that the images have been saved to the mobile computing device 110 can be provided to the user.

Alternatively, if a user selects the option limiting the review to flagged images only, at 248, the user can select the month/year, day, and/or upload on that day for viewing of flagged images. At 250, the stored images can be viewed, with the option of saving the one or more images to the mobile computing device 110.

If the user selects the option of comparing two or more images, at 252A-B, the user can select the foot (e.g., left foot or right foot), month/year, day, and/or upload on that day of the images to be compared. At 254, the stored images can be viewed, with the option of saving the one or more images to the mobile computing device 110.

Minor observable changes in a condition of the plantar surface, particularly in comparison to past images, can serve as an indication that further review by a clinician may be desirable. Where further review by a clinician is desirable, the user can send a notification to a remote display 118, where the clinician can review the stored, flagged and/or compared images within the cloud computing platform 114.

In one embodiment, the foot screening system 100 can utilize one or more automatic image analysis methods, for example via a deep learning algorithm (e.g., a convolution neural network, or the like), as an aid to healthcare workers in the screening of a skin condition of a foot of a patient for sores, ulcers, or other symptoms of disease. In some embodiments, the one or more automatic analysis methods can be configured to rapidly compare current images of a user's foot to past images of the user's foot, or an amalgamation of many foot images. Accordingly, in some embodiments, the automatic image analysis method can assist in assessment of a state of the user's foot, and to flag images for further review by healthcare provider. Further, where a sore, ulcer, or other symptom of disease is detected, the automatic image analysis method can assist in determining a wound perimeter, area, and/or volume as an aid in monitoring the status of a known wound.

Figure 14A:
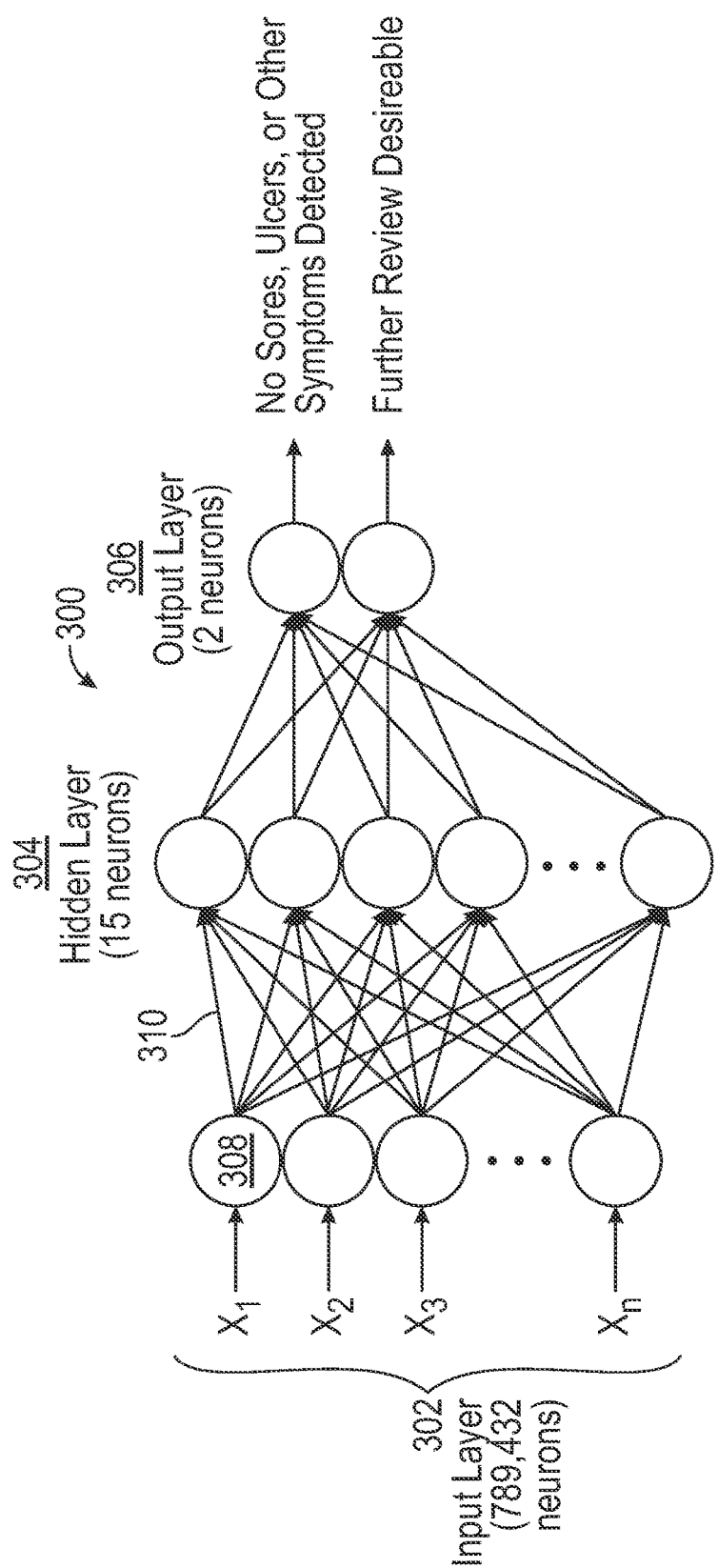
FIG. 14A is a network diagram depicting a neural network, in accordance with an embodiment of the disclosure.

For example, with reference to FIG. 14A, in one embodiment, the automatic image analysis method can comprise a neural network 300, including an input layer 302, one or more hidden layers 304, and an output layer 306. Each of the layers 302, 304, and 306 can include a corresponding plurality of neurons 308. Although only a single hidden layer 304 is depicted, it is contemplated that the neural network 300 can include multiple hidden layers 304.

The inputs for the input layer can be a number between 0 and 1. For example, in one embodiment, the input layer 302 can include a total of 786,432 neurons corresponding to a 1024×768 pixel output of a camera unit, wherein each of the input values is based on an RGB color code between the value of 0 and 1. In another embodiment, the input layer 320 can include three layers of inputs for each pixel, wherein each of the input values is based on a color code between the value of 0 and 1 for each of the R, G, and B colors; other quantities of neurons and input values are also contemplated.

Each of the neurons 308 in one layer (e.g., input layer 302) can be connected to each of the neurons 308 of the subsequent layer (e.g., hidden layer 304) via a connection 310, as such, the layers of the network can be said to be fully connected. Although it is also contemplated that the algorithm can be organized as a convolutional neural network, wherein a distinct group of input layer 302 neurons (e.g., representing a local receptive field of input pixels) can couple to a single neuron in a hidden layer 304 via a shared weighted value.

Figure 14B:
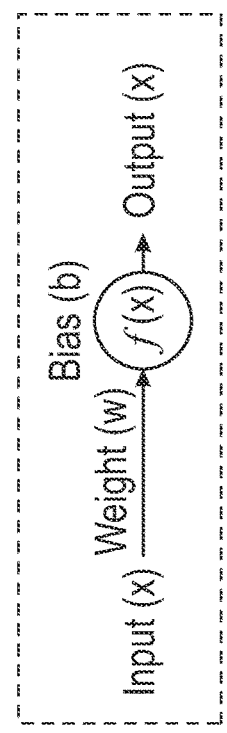
FIG. 14B depicts a single neuron within the neural network of FIG. 14A, in accordance with an embodiment of the disclosure.

With additional reference to FIG. 14B, each of the neurons 308 can be configured to receive one or more input values (x) and compute an output value (y). In fully connected networks, each of the neurons 308 can be assigned a bias value (b), and each of the connections 310 can be assigned a weight value (w). Collectively the weights and biases can be tuned as the neural network 300 learns how to correctly classify detected objects. Each of the neurons 308 can be configured as a mathematical function, such that an output of each neuron 308 is a function of the connection weights of the collective input, and the bias of the neuron 308, according to the following relationship:

$$y = w \cdot x + b$$

In some embodiments, output (y) of the neuron 308 can be configured to take on any value between 0 and 1. Further, in some embodiments the output of the neuron 308 can be computed according to one of a linear function, sigmoid function, tanh function, rectified linear unit, or other function configured to generally inhibit saturation (e.g., avoid extreme output values which tend to create instability in the network 300).

In some embodiments, the output layer 306 can include neurons 308 corresponding to a desired number of outputs of the neural network 300. For example, in one embodiment, the neural network 300 can include a plurality of output neurons dividing the plantar surface of the foot into a number of distinct regions in which the likelihood of the presence of a sore can be indicated with an output value of between 0 and 1. Other quantities of output neurons are also contemplated; for example, the output neurons could correspond to object classifications (e.g., comparison to a database of historical images), in which each output neuron would represent a degree of likeness of the present image to one or more historical images. In a different example, the number of output neurons is equal to the levels of severity of a wound classification system.

The goal of the deep learning algorithm is to tune the weights and balances of the neural network 300 until the inputs to the input layer 302 are properly mapped to the desired outputs of the output layer 306, thereby enabling the algorithm to accurately produce outputs (y) for previously unknown inputs (x). For example, if the vision system captures a digital image of a plantar surface of the user's foot (the pixels of which are fed into the input layer), a desired output of the neural network 300 would be the indication of whether further analysis by healthcare provider is desirable. In some embodiments, the neural network 300 can rely on training data (e.g., inputs with known outputs) to properly tune the weights and balances.

In tuning the neural network 300, a cost function (e.g., a quadratic cost function, cross entropy cross function, etc.) can be used to establish how close the actual output data of the output layer 306 corresponds to the known outputs of the training data. Each time the neural network 300 runs through a full training data set can be referred to as one epoch. Progressively, over the course of several epochs, the weights and balances of the neural network 300 can be tuned to iteratively minimize the cost function.

Effective tuning of the neural network 300 can be established by computing a gradient descent of the cost function, with the goal of locating a global minimum in the cost function. In some embodiments, a backpropagation algorithm can be used to compute the gradient descent of the cost function. In particular, the backpropagation algorithm computes the partial derivative of the cost function with respect to any weight (w) or bias (b) in the network 300. As a result, the backpropagation algorithm serves as a way of keeping track of small perturbations to the weights and biases as they propagate through the network, reach the output, and affect the cost. In some embodiments, changes to the weights and balances can be limited to a learning rate to prevent overfitting of the neural network 300 (e.g., making changes to the respective weights and biases so large that the cost function overshoots the global minimum). For example, in some embodiments, the learning rate can be set between about 0.03 and about 10. Additionally, in some embodiments, various methods of regularization, such as L1 and L2 regularization, can be employed as an aid in minimizing the cost function.

Accordingly, in some embodiments, the foot screening system 100 be configured to utilize pixel data from a mobile computing device 110 as an input for the cloud computing platform 114/database 116 configured to operate a deep learning algorithm for the purpose of automatically assigning a probability that objects viewed by the mobile computing device 110 warrant further review by healthcare provider. Although the present disclosure specifically discusses the use of a deep learning algorithm in the form of a neural network 300 to establish plantar surface wound probabilities, other methods of automatic recognition and classification are also contemplated.

Further, in some embodiments, the neural network 300 can be configured to utilize image data falling outside of the visible light spectrum. For example, in some embodiments, a mobile computing device 110 with light detection and ranging (LiDAR), thermal imaging, infrared (IR), and other near visible light spectrum capabilities can be utilized to capture images of the plantar surface of a user's foot. Thereafter, the image data can be analyzed by the neural network 300 as an aid in the detection of the formation of ulcers or other sores before their emergence becomes visually detectable. Alternatively, in some embodiments, method and system can be performed with an imaging device having native hyperspectral imaging capabilities. In some embodiments, two or more images (e.g., an IR image and a traditional image) can be amalgamated to form a single image of the plantar surface of a foot having characteristics of the best features of each of the images in the combined single amalgamated image.

Various embodiments of systems, devices, and methods have been described herein. These embodiments are given only by way of example and are not intended to limit the scope of the claimed inventions. It should be appreciated, moreover, that the various features of the embodiments that have been described can be combined in various ways to produce numerous additional embodiments. Moreover, while various materials, dimensions, shapes, configurations and locations, etc. have been described for use with disclosed embodiments, others besides those disclosed can be utilized without exceeding the scope of the claimed inventions.

Persons of ordinary skill in the relevant arts will recognize that the subject matter hereof can comprise fewer features than illustrated in any individual embodiment described above. The embodiments described herein are not meant to be an exhaustive presentation of the ways in which the various features of the subject matter hereof can be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim can refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that the individual steps used in the methods of the present teachings can be performed in any order and/or simultaneously, as long as the teaching remains operable. Furthermore, it should be understood that the apparatus and methods of the present teachings can include any number, or all, of the described embodiments, as long as the teaching remains operable.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of screening a segment of a lower extremity of a user for skin disturbances, wounds, ulcers, and other signs of disease, the method comprising:
   positioning at least a portion of the segment of a lower extremity of the user on a lower extremity support platform;
   activating a foot screening assist program on a user interface of a mobile computing device;
   positioning the mobile computing device on a camera stabilizer platform;
   providing an initiation command as a voice command to the foot screening assist program executing on the mobile computing device to initiate a capture of one or more digital images of at least a portion of the segment of the lower extremity of the user;
   retrieving the mobile computing device from the camera stabilizer platform; and
   storing the one or more digital images in a database for comparison of the one or more digital images to previous images of the segment of the lower extremity of the patient or for further review by a clinician.

2. The method of claim 1, wherein the initiation command includes causing the foot screening assist program to accept a first voice command to initiate a first image capture sequence, and causing the foot screening assist program to accept a second voice command to initiate a second image capture sequence.

3. The method of claim 1, wherein the foot screening assist program is configured to provide a user interface on a visual display of the mobile computing device and to cause the user interface to display the one or more digital images of the segment of the lower extremity, including a plantar surface of a foot of the user, for review, augmentation or annotation of the images by the user, and wherein the method further comprises adding user observational data, annotation data, additional images or additional data to the one or more digital images via the user interface.

4. The method of claim 1, further comprising causing the foot screening assist program to provide audible instructions to the user for capturing the one or more images of the segment of the lower extremity of the user.

5. The method of claim 4, wherein the method further comprises causing the foot screening assist program to provide an audible instruction of a recommended spacing between the lower extremity support platform and the camera stabilizer platform.

6. The method of claim 5, wherein the lower extremity support platform and the camera stabilizer platform are operably coupled to one another via one or more extension rods, and wherein the method further comprises causing the foot screening assist program to provide an audible instruction of spacing recommendations for the lower extremity support platform and the camera stabilizer platform at one or more distances based on one or more of a set of optical characteristics of the mobile computing device and a set of physical parameters of the camera stabilizer platform.

7. The method of claim 1, wherein the capture of the one or more images generates a plurality of captured images, and wherein the method further comprises causing the foot screening assist program to compare two or more of the plurality of captured images.

8. The method of claim 1, wherein the capture of the one or more images generates a plurality of captured images and wherein the plurality of captured images includes non-visible data falling outside of the visible light spectrum, and wherein the method further comprises utilizing the non-visible data in evaluating the plurality of captured images to identify a potential wound on the segment of the lower extremity of the user before an emergence of the wound becomes visually detectable.

9. The method of claim 1, wherein the capture of the one or more images generates a plurality of captured images, and wherein the method further comprises utilizing a neural network to aid in a classification of the plurality of captured images.

10. The method of claim 1, wherein the capture of the one or more images generates a plurality of captured images and wherein the lower extremity support platform includes a standardization indicator, and wherein the method further comprises causing utilization of the standardization indicator in processing the plurality of captured images.

11. A foot screening system configured to aid in a screening of a distal portion of a lower extremity, including a plantar surface of a foot of a user for skin disturbances, wounds, ulcers, and other signs of disease, the foot screening system comprising:
  a camera stabilizer platform configured to support a mobile computing device at a desired angle and distance from the lower extremity stabilization structure;
  a lower extremity stabilization structure providing a foot platform operably coupled to the camera stabilizer platform, the foot platform configured to provide direct support of only one of a toe or a heel of the foot of the user during the screening; and
  a screening assist program configured to operate on a mobile computing device having a user interface, the screening assist program being configured for:
    activating the screening assist program on the user interface after which the mobile computing device is positioned on the camera stabilizer platform;
    accepting an initiation command consisting of a voice command to remotely initiate a capture of one or more digital images of the lower extremity of the user by the mobile computing device; and
    storing the one or more digital images in a database accessible for visual comparison of the one or more digital images to previous images of the lower extremity of the user.

12. The system of claim 11, wherein the camera stabilizer platform configured to enable angular adjustment of a mobile computing device support surface relative to a horizontal frame of reference.

13. The system of claim 12, wherein the foot platform is operably coupled to the camera stabilizer platform by one or more extension rods, and wherein the screening assist program is further configured to provide an audible instruction of spacing recommendations for the lower extremity stabilization structure and the camera stabilizer platform at one or more distances based on one or more of a set of optical characteristics of the mobile computing device and a set of physical parameters of the camera stabilizer platform.

14. The system of claim 13, wherein the foot platform includes a foot contacting structure on a top surface of the foot platform adapted to support a foot of the user a distance above the top surface of the foot platform.

15. The system of claim 14, wherein the foot platform includes a material cutout in a side of the platform configured to house at least a portion of the camera stabilizer platform in a collapsed, storage position.

16. The system of claim 14, wherein the foot platform includes a standardization indicator, and wherein the screening assist program is configured to utilize the standardization indicator in processing the plurality of captured images.

17. The system of claim 12, wherein the lower extremity stabilization structure comprises a wheelchair, and wherein the screening assist program is further configured to provide spacing recommendations for the camera stabilizer platform relative to the wheelchair at one or more distances based on one or more of a set of optical characteristics of the mobile computing device and a set of physical parameters of the camera stabilizer platform.

18. The system of claim 11, wherein the screening assist program is configured to accept a first voice command to initiate a first image capture sequence, and a second voice command to initiate a second image capture sequence.

19. The system of claim 11, wherein the screening assist program is further configured to display the one or more digital images on the user interface for review, augmentation or annotation of the images by the user, and input and store user observational data, annotation data, additional images or additional data as associated with the one or more digital images.

20. The system of claim 11, wherein the capture of the one or more images is configured to generate a plurality of captured images at least one of which includes non-visible data falling outside of the visible light spectrum, and wherein the non-visible data is utilized in evaluating the plurality of captured images to identify a potential wound on the plantar surface of the foot of the user before an emergence of the wound becomes visually detectable.

21. A method of screening a plantar surface of a foot of a user for skin disturbances, wounds, ulcers, and other signs of disease, the method comprising:
  positioning a distal portion of a lower extremity of the user on a foot platform configured to provide direct support of only one of a toe or a heel of the foot of the user during the screening;
  providing a remote initiation command consisting of at least one of a voice command, an auditory signal, a Bluetooth remote signal, or a Wi-Fi signal to an imaging source positioned at least one of on or in a camera stabilization platform operably coupled to the foot platform to initiate a capture of one or more digital images of a plantar surface of a foot of the user; and
storing the one or more digital images in a database for comparison of the one or more digital images to previous images of the plantar surface of the foot of the patient or for further review by a clinician.

22. A foot screening system configured to aid in screening a plantar surface of a foot of a user for skin disturbances, wounds, ulcers, and other signs of disease, the foot screening system comprising:
  a foot platform including a foot contacting structure on a top surface of the foot platform adapted to provide direct support of only one of a toe or a heel of a foot of the user a distance above the top surface of the foot platform;
  a camera stabilizer platform including an angularly adjustable support surface configured to selectively support a mobile computing device at a desired angle relative to a horizontal frame of reference and an adjustable extension mechanism operably coupled to the foot platform and configured to selectively position the camera stabilizer platform at a desired distance from the foot platform; and
  a screening assist program configured to operate on a user interface of the mobile computing device, the screening assist program being configured to:
    activate the screening assist program on the user interface;
    provide instructions to position the mobile computing device on the camera stabilizer platform and the foot of the user on the foot platform and to make any adjustments of the desired angle and desired distance of camera stabilizer platform relative to the foot platform based in part on an image of the foot of the user as imaged by at least one camera in the mobile computing device;
    accept an initiation command consisting of at least one of a voice command, an auditory signal, a Bluetooth remote signal, or a Wi-Fi signal to remotely initiate a capture of one or more digital images of the foot of the user by the mobile computing device;
    provide instructions to retrieve the mobile computing device from the camera stabilizer platform;
    store the one or more digital images in a database accessible for comparison of the one or more digital images to previous images of the foot of the user;
    display the one or more digital images on the user interface for review, augmentation or annotation of the one or more digital images to be input and stored as observational data, annotation data, additional images or additional data associated with the one or more digital images in the database.

23. The system of claim 22, wherein the foot platform includes a material cutout in a side of the platform configured to house at least a portion of the camera stabilizer platform in a collapsed, storage position.

24. The system of claim 23, wherein the camera stabilization platform is extendable coupled to the foot platform via one or more telescoping extension rods configured to enable the camera stabilization platform and foot platform to transition between the collapsed, storage position in which the camera stabilization platform is at least partially housed within the foot platform, and an expanded, in use position, in which the camera stabilization platform is positioned at an adjustable distance from the foot platform, wherein in the collapsed, storage position a portion of the camera stabilization platform protrudes from the foot platform to allow the user ease in adjusting the camera stabilization platform position.

25. The system of claim 23, wherein the foot platform includes a handle extending from the top surface of the foot platform to serve as a carrying handle, and wherein the handle folds into the plane of the top surface of the foot platform while not being carried.

26. The method of claim 22, wherein the foot platform includes a frustum extending from the top surface of the foot platform configured to support only one of the toe or the heel of the foot of the user.

* * * * *